(12) United States Patent
Fladoos

(10) Patent No.: US 10,913,241 B2
(45) Date of Patent: Feb. 9, 2021

(54) FLEXIBLE ADHESIVE TAPE FOR HEATING BEVERAGES, PIPES AND OTHER ARTICLES

(71) Applicant: Jason Fladoos, Santa Monica, CA (US)

(72) Inventor: Jason Fladoos, Santa Monica, CA (US)

( * ) Notice: Subject to any disclaimer, the term of this patent is extended or adjusted under 35 U.S.C. 154(b) by 0 days.

(21) Appl. No.: 16/418,984

(22) Filed: May 21, 2019

(65) Prior Publication Data

US 2020/0254722 A1 Aug. 13, 2020

Related U.S. Application Data

(63) Continuation-in-part of application No. 16/184,188, filed on Nov. 8, 2018, now Pat. No. 10,342,889, and a continuation-in-part of application No. 16/120,651, filed on Sep. 4, 2018, now Pat. No. 10,350,109, and a continuation-in-part of application No. 16/022,569, filed on Jun. 28, 2018, now Pat. No. 10,492,957.

(51) Int. Cl.

| | |
|---|---|
| *A61B 18/06* | (2006.01) |
| *B32B 7/12* | (2006.01) |
| *B32B 29/00* | (2006.01) |
| *C09J 7/35* | (2018.01) |
| *C09J 7/38* | (2018.01) |

(52) U.S. Cl.
CPC ............... *B32B 7/12* (2013.01); *A61B 18/06* (2013.01); *B32B 29/002* (2013.01); *C09J 7/35* (2018.01); *C09J 7/38* (2018.01); *B32B 2405/00* (2013.01)

(58) Field of Classification Search
CPC ....... A41B 11/003; A41B 11/004; B32B 7/12; F25D 3/08; A61B 18/06

USPC ............................................ 62/277; 126/204
See application file for complete search history.

(56) References Cited

U.S. PATENT DOCUMENTS

| | | | | |
|---|---|---|---|---|
| 5,431,622 A | * | 7/1995 | Pyrozyk | A61F 13/0203 602/2 |
| 5,792,213 A | * | 8/1998 | Bowen | A61F 7/03 607/114 |
| 6,036,004 A | | 3/2000 | Bowen | |
| 9,510,972 B2 | * | 12/2016 | Badawi | A61F 9/0008 |
| 9,702,609 B2 | * | 7/2017 | Robb | F25D 3/08 |
| 2002/0052569 A1 | * | 5/2002 | Horning | A61F 7/10 602/41 |
| 2005/0080368 A1 | * | 4/2005 | Hurwitz | A61F 13/0203 602/2 |

(Continued)

*Primary Examiner* — Kim M Lewis
(74) *Attorney, Agent, or Firm* — William J. Benman; Benman. Brown & Williams

(57) ABSTRACT

A heating tape and heating pad. In a most general embodiment, the inventive tape includes a first layer of thermally conductive material; a second layer of thermal insulation; and a third layer of exothermic material, sandwiched between the first and second layers. The third layer is constructed with reactants effective to cause an exothermic chemical reaction. In a first embodiment, the invention provides a beverage heating device. In a second embodiment, the invention provides a pipe heating device. The heating pad is implemented with a first layer of thermally conductive material; a second layer of material providing a base; and a third layer of exothermic material, sandwiched between the first and second layers. In the illustrative embodiment, the third layer has a contour effective to create suction whereby the pad adheres to a surface to be heated.

8 Claims, 4 Drawing Sheets

(56) References Cited

U.S. PATENT DOCUMENTS

| | | | |
|---|---|---|---|
| 2006/0282138 A1* | 12/2006 | Ota | A61F 7/03 607/96 |
| 2008/0147153 A1* | 6/2008 | Quincy | A61F 7/03 607/114 |
| 2008/0178865 A1* | 7/2008 | Retterer | F25D 5/02 126/263.08 |
| 2014/0166672 A1* | 6/2014 | Stroucken | A47G 23/0313 220/592.01 |
| 2014/0257155 A1* | 9/2014 | Altinok | A61H 39/04 602/1 |

* cited by examiner

FLEXIBLE ADHESIVE TAPE FOR HEATING BEVERAGES, PIPES AND OTHER ARTICLES

REFERENCE TO PRIOR APPLICATION

This application is a continuation-in-part of U.S. Patent application entitled FLEXIBLE ADHESIVE PHYSIO TAPE WITH THERMAL PROPERTIES filed by J. Fladoos on Jun. 28, 2018, Ser. No. 16/022,569 the teachings of which are hereby incorporated herein by reference.

BACKGROUND OF THE INVENTION

Field of the Invention

The present invention relates to tapes and bindings. More specifically, the present invention relates to systems and methods for heating beverages, pipes and other articles.

Description of the Related Art

Numerous methods and apparatus are known in the art for heating containers, conduits and the fluids, gases and solids therein. For containers such as bottles and cans, ovens, stoves, microwaves, hot plates and the like are widely used. However, these devices are generally unable to sustain an optimal temperature of the fluids or gases after removal of the container and not available for pipes and conduits.

Heating tape is known in the art but conventional heat tape is generally implemented with electrically driven coils. As a result, conventional heat tape is impractical and too expensive for simple beverage heating applications.

The parent application (U.S. patent application entitled FLEXIBLE ADHESIVE PHYSIO TAPE WITH THERMAL PROPERTIES filed by J. Fladoos on Jun. 28, 2018, Ser. No. 16/022,569 the teachings of which are hereby incorporated herein by reference (now issued as U.S. Pat. No. 10,492,957), the teachings of which are incorporated herein by reference, teaches a heating physio tape for heating human tissue. While this patent mentions in passing that such a construction could be adapted for heating beverage containers, a detailed teaching is not provided.

Hence, there is a need in the art for a simple, effective, fast acting, portable, low cost beverage heating device.

SUMMARY OF THE INVENTION

The need in the art is addressed by the heating tape and heating pad of the present invention. In a most general embodiment, the inventive tape includes a first layer of thermally conductive material; a second layer of thermal insulation; and a third layer of exothermic material, sandwiched between the first and second layers. The third layer is constructed with reactants effective to cause an exothermic chemical reaction.

In the illustrative embodiment, the third layer is fabricated with cellulose, iron, water, activated carbon, vermiculite and salt. In a specific embodiment, a breakable barrier in the third layer separates the reactants so the heating can be initiated at any point by breaking the barrier. The third layer could include multiple layers saturated or interwoven with reactants.

In a first alternative embodiment, the invention provides a beverage heating device. In a second embodiment, the invention provides a pipe heating device.

The beverage heating device can be implemented as a heating pad with a first layer of thermally conductive material; a second layer of material providing a base which may or may not include material providing thermal insulation to protect the object that the heating pad is set on; and a third layer of exothermic material, sandwiched between the first and second layers.

In the illustrative embodiment, at least one of the layers has a contour effective to create suction whereby the pad adheres to a surface to be heated or this layer may also have adhesive to stick to the surface of the object being heated. The contour also provides a space for reactants to fit under the concave bottom of the bottle or can.

BRIEF DESCRIPTION OF THE DRAWINGS

FIG. 3b is a sectional end view of the tape depicted in FIG. 3a.

FIG. 3c is a sectional side view of the tape depicted in FIG. 3a.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
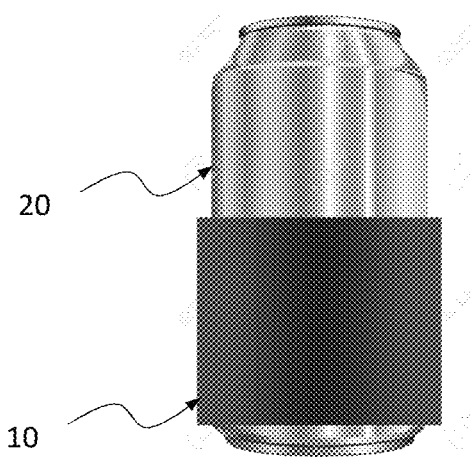
FIG. 1 is perspective view of the heating tape of the present invention mounted on a beverage container in accordance with an illustrative embodiment of the invention.

FIG. 1 is perspective view of the heating tape 10 of the present invention mounted on a beverage container 20 in accordance with an illustrative embodiment of the invention.

Figure 2:
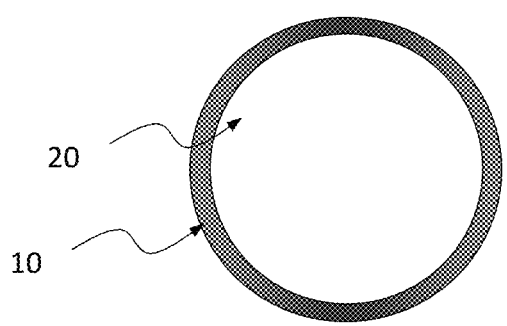
FIG. 2 is a top view of the heating tape of FIG. 1.

FIG. 2 is a top view of the heating tape 10 of FIG. 1 mounted on the beverage container 20.

Figure 3A:
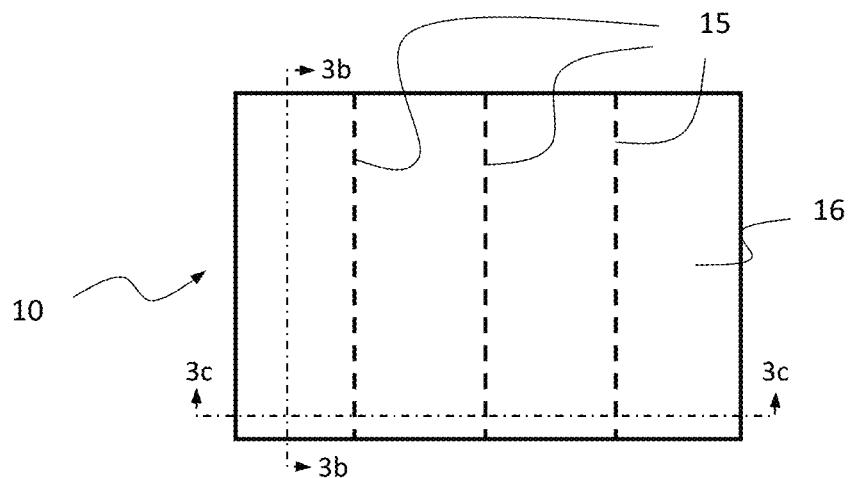
FIG. 3a is top schematic view of an illustrative embodiment of the heating tape of the present invention.

FIG. 3a is top schematic view of an illustrative embodiment of the heating tape 10 of the present invention.

Figure 3B:
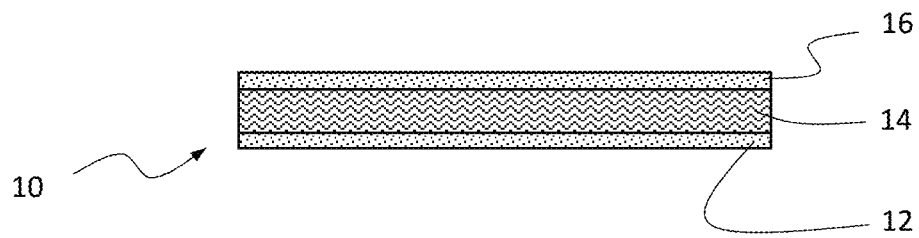

FIG. 3b is a sectional end view of the tape depicted in FIG. 3a.

Figure 3C:
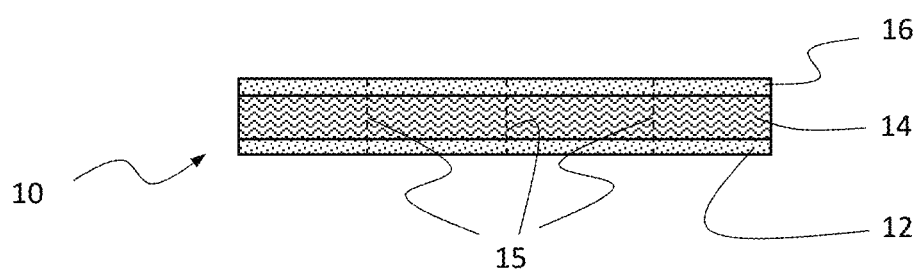

FIG. 3c is a sectional side view of the tape depicted in FIG. 3a.

As illustrated in FIGS. 3a-c, the inventive tape includes a first layer 12 of thermally conductive material; a second layer 16 of thermal insulation; and a third layer 14 of exothermic material, sandwiched between the first and second layers 12 and 16 respectively.

The first layer 12 may be made of porous or non porous fabric with or without elastic properties, plastic, biodegradable plastic (made of corn starch or other traditional petrochemical), rubber, metal, PTFE, or Teflon. The second layer 16 may be plastic, biodegradable plastic (made of corn starch or other traditional petrochemical), rubber, metal, PTFE, or Teflon.

The third layer 14 is constructed with reactants effective to cause an exothermic chemical reaction. In an illustrative embodiment, with the modifications taught herein, the device 10 may be implemented in accordance with the teachings of U.S. Pat. No. 6,036,004 issued Mar. 14, 2000 to M. L. Bowen entitled MULTI-COMPARTMENT BAG WITH BREAKABLE WALLS, the teachings of which are hereby incorporated herein by reference.

In the illustrative embodiment, the reactants are dry, solid compounds such as cellulose, iron, water, activated carbon, vermiculite and salt. In this embodiment, the tape is activated by breaking a barrier (not shown) separating water filled chambers and chambers with one or more of the above-mentioned dry compounds, allowing them to mix initiating an exothermic reaction.

In another implementation, the chambers may be filled with a supersaturated solution of sodium acetate in water. In this case, crystallization is triggered by flexing a small flat disc of notched ferrous metal embedded in the liquid. Pressing the disc releases very tiny adhered crystals of sodium acetate into the solution which then act as nucleation sites for the crystallization of the sodium acetate into the hydrated salt (sodium acetate trihydrate, $CH_3COONa.3H_2O$). Because the liquid is supersaturated, this makes the solution crystallize suddenly, thereby releasing the energy of the crystal lattice.

In a multi-use/reusable embodiment of the present teachings, heat is produced by mixing a chemical salt in dry crystal form with water. By way of example, suitable dry chemical salt examples include calcium chloride, magnesium sulfate and sodium acetate however the invention is not limited thereto. The solution is super saturated meaning it has been heated to dissolve more salt. When an internal metal strip (usually stainless steel) is bent, tiny particles of metal are released which offer nucleation sites causing crystals to form releasing the stored heat energy of the solution.

There are multiple ways to vary the intensity and/or duration of the heating/cooling. For example, changing the concentration and/or quantity of the reactants would control the duration of heat and also the intensity. This allows for multiple choices of the thermal tape depending on the environment and length of time heating or cooling is desired.

In a specific embodiment, a breakable barrier (not shown) in the third layer 14 separates the reactants so the heating can be initiated at any point by breaking the barrier. The third layer 14 could include multiple layers saturated or interwoven with reactants.

The tape is adapted for activation by breaking a barrier separating water filled chambers and chambers with one or more of the dry compounds, allowing them to mix to initiate the exothermic reaction.

The third layer 14 could be implemented as a powder or crystal or implemented as a liquid in which case the third layer has sealed borders.

As illustrated in FIG. 3a, the third layer can be implemented with segmented lengths of exothermic reactants to allow for the tape to be cut at various lengths without cutting through a layer of reactants. The segments are separated by cutting or tearing along the seams 15 depicted in FIG. 3a.

Figure 4A:
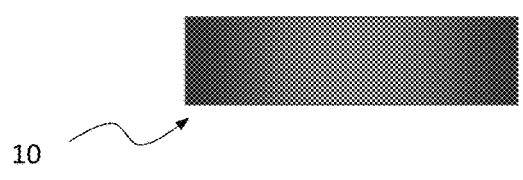
FIG. 4a is an elevated side view of an illustrative embodiment of the tape of the present invention implemented as an elastic ring.

The tape may be implemented as a ring or strip with various fasteners as illustrated in FIGS. 4a-d. FIG. 4a, for example, is an elevated side view of an illustrative embodiment of the tape of the present invention implemented with elastic layers to provide an elastic ring.

Figure 4B:
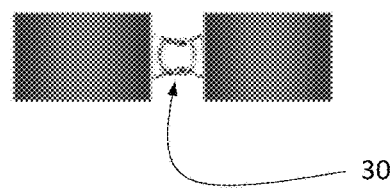
FIG. 4b is an elevated side view of an alternative embodiment of the tape of the present invention implemented with a hook type fastener.

FIG. 4b is an elevated side view of an alternative embodiment of the tape of the present invention implemented with a hook type fastener 30.

Figure 4C:
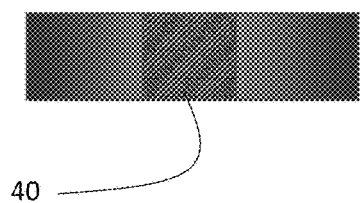
FIG. 4c is an elevated side view of a second alternative embodiment of the tape of the present invention implemented with a hook and loop type fastener.

FIG. 4c is an elevated side view of a second alternative embodiment of the tape of the present invention implemented with a hook and loop (aka VELCRO®) type fastener 40.

Figure 4D:
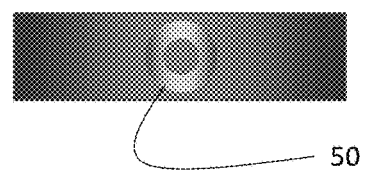
FIG. 4d is an elevated side view of third alternative alternative embodiment of the tape of the present invention implemented with a snap type fastener.

FIG. 4d is an elevated side view of third alternative embodiment of the tape of the present invention implemented with a snap type fastener 50. All of the above described fasteners may be made of plastic, biodegradable plastic (made of corn starch or other traditional petrochemical), metal or other suited material.

For pipe heating applications, the tape may be wrapped in a spiral pattern around the pipe and secured in place with adhesive material provided on layers 12 and 16. In this case, the tape 10 is designed for activation upon a tight wrapping of the tape around the pipe. Various embodiments would be made to accommodate pipes of various sizes and to effect activation upon proper application thereto.

Figure 5:
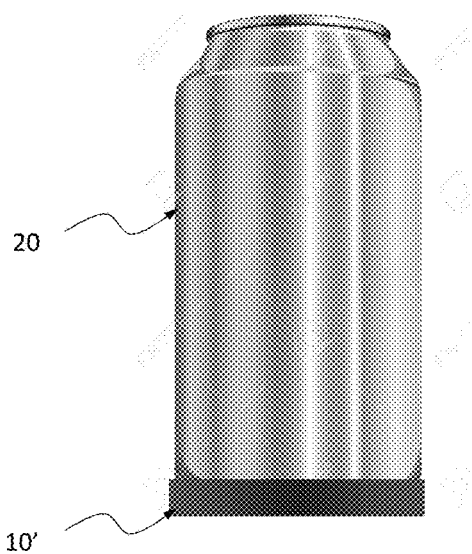
FIG. 5 is perspective view of the heating pad of the present invention mounted under a beverage container in accordance with an illustrative embodiment of the invention.
Figure 5A:
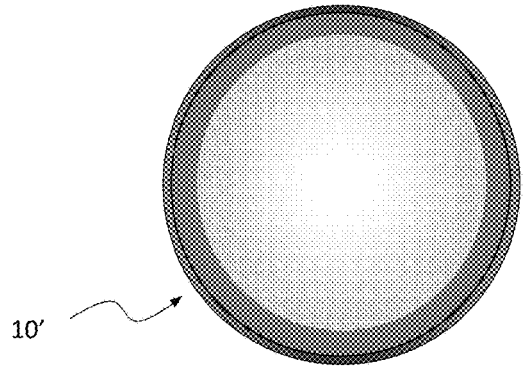
FIG. 5a is a top plan view of the pad depicted in FIG. 4.
Figure 5B:
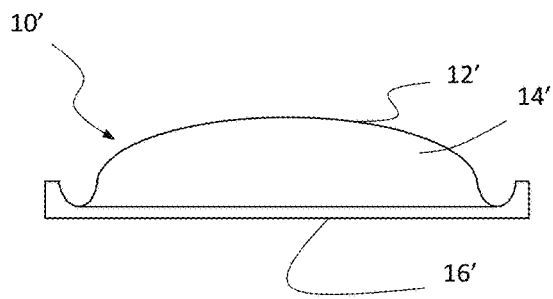
FIG. 5b is a sectional side view of the pad depicted in FIG. 4.

FIG. 5 is perspective view of the heating pad of the present invention mounted under a beverage container in accordance with an illustrative embodiment of the invention. FIG. 5a is a top plan view of the pad depicted in FIG. 4. FIG. 5b is a sectional side view of the pad depicted in FIG. 4.

As illustrated in FIGS. 5, 5a and 5b, in accordance with the present teachings, a beverage heating device can be implemented as a heating pad 10' with a first layer of thermally conductive material 12'; a second layer of material 16' providing a base which may or may not include material providing thermal insulation to protect the object that the heating pad is set on; and a third layer of exothermic material 14', sandwiched between the first and second layers 12' and 16' respectively.

In the best mode, the first layer 12' is metallic foil, plastic, or other suitable thermally conductive material and the base layer 16' is plastic or rubber or other suitably rigid material, with or without adhesive properties, depending on the attributes desired or required for a given application.

As illustrated in FIGS. 5a and 5b, in the illustrative embodiment, the third layer 14' has a contour effective to create suction whereby the pad 10' adheres to a surface to be heated. In FIG. 5b, the contour is dome shaped in contemplation of a beverage can 20 with a concave bottom surface.

The inventive tape 10 may be fabricated by applying a strong adhesive such as zinc oxide or other suitable adhesive to a large sheet of high quality porous fabric 16 such as a blend of cotton, latex and/or nylon.

Next, the top layer 12, fabricated in the same manner as the bottom layer 16, is applied to the exothermic layer 14. The top and bottom layers 12 and 16 may be 97% tightly woven elasticated cotton with 3% nylon fibers or implemented with a ratio of cotton or nylon better suited for a particular application. The top and bottom layers 12 and 16 may also be constructed without any elastic properties and with or without adhesive properties depending on what it is being applied to. The first layer 12 may be made of porous or non porous fabric with or without elastic properties, plastic, biodegradable plastic (made of corn starch or other traditional petrochemical), rubber, metal, PTFE or Teflon. The second layer 16 may be plastic, biodegradable plastic (made of corn starch or other traditional petrochemical), rubber, metal, PTFE or Teflon.

In an alternative embodiment, a hollow section of the tape 10 could be provided and filled with a pre-made, plastic, enclosed tube of reactants. This eliminates the need for the tape to be leak proof. This also simplifies the manufacturing process as the tape can be made with a hollow core and then tubes can be inserted that are filled with reactants that heat. Those tubes can also be filled with varying quantities depending on the desired intensity of heat.

In another alternative embodiment, the pad 10 could be constructed so when a can or bottle is placed and pressed on top of the dome 16 a barrier is broken from the pressure to activate the reaction of heating the can or bottle.

In yet another alternative embodiment, multiple cooling pads 10 could be connected within one large pad with six domes to enable the cooling of multiple cans at once. For practical purposes you could set a six pack of cans on top of a pad with six domes. Each pad could be activated by the pressure of each can or a central water chamber barrier could be broken to activate each pad segment via water as a catalyst.

Structure of the Heat Tape:

The tape may be constructed in multiple ways. The tape may be constructed to contain hollow chambers that can hold and separate the individual reactants.

In accordance with the present invention, individual reactants can either be enclosed in a flexible, leak-proof container that will fit into each chamber of the tape or the tape can be constructed of leak-proof material so the raw reactants can be placed directly inside each chamber. In either aspect, there will have to be a breakable barrier that separates the reactants, so the heating can be initiated at any point by breaking the barrier.

The tape could also be constructed with multiple layers of pre-made reactant strips that are stacked or glued onto each other but separated by a barrier. Squeezing the tape by hand could break the barriers and initiate the exothermic reaction.

Practical Uses and Temperature Ranges:

Tape being adhered to an inanimate object can be made as hot as needed depending on the desired outcome. Another practical use is to heat up a frozen pipe and melt the ice that is preventing the flow of water. Again, the reactants can be adjusted to obtain the desired temperature and length of heating time.

Dimensions of the Heat Tape:

In the best mode, the tape has a width of 1-6 inches, a thickness of 1-40 mm and a length of 3 inches to any length. The tape can be manufactured to have segmented lengths of exothermic reactants to allow for the tape to be cut at various lengths without cutting through the container, pouch or layer of reactants.

Those of ordinary skill in the art will appreciate that the present invention is not limited to the fabrics and chemicals disclosed herein. Other combinations of fabrics and chemicals may be employed without departing from the scope of the present teachings. For example, a plurality of small capsules may be provided within the tape which, when squeezed by a user, ruptures and releases a mix of chemicals leading to an exothermic heating effect.

Those having ordinary skill in the art and access to the present teachings will recognize additional modifications, applications and embodiments within the scope thereof.

It is therefore intended by the appended claims to cover any and all such applications, modifications and embodiments within the scope of the present invention.

The invention claimed is:

1. A heating tape consisting of:
   a first layer of material consisting of a porous fabric comprising a blend of cotton, latex and/or nylon;
   a second layer of porous fabric consisting of a blend of cotton, latex and/or nylon material; and
   a third layer of exothermic material sandwiched between the first and second layers comprising a hollow chamber, wherein the hollow chamber comprises pre-made enclosed tubes of reactants effective to cause an exothermic chemical reaction,
   wherein the tape is flexible and configured for activation upon a tight wrapping thereof around an object to be heated.

2. The tape of claim 1 wherein the reactants are cellulose, iron, water, activated carbon, vermiculite and salt.

3. The tape of claim 2 wherein the reactants are adapted for activation by breaking water filled tubes and tubes filled with the remaining reactants, allowing them to mix to initiate the exothermic reaction.

4. The tape of claim 1 wherein the tubes are flexible leak-proof containers.

5. The tape of claim 1 wherein the third layer has segmented lengths to allow for the tape to be cut at various lengths without cutting through the reactants.

6. The tape of claim 1 wherein the tubes are filled with a supersaturated solution of sodium acetate or other suitable chemical salt and water.

7. The tape of claim 6 wherein the tubes further include a small flat disc of notched ferrous metal embedded in the water for flexing and triggering crystallization.

8. The tape of claim 1 wherein the tape has a width of 1-6 inches, a thickness of 1-40 mm.

* * * * *